United States Patent [19]
Hotta et al.

[11] 4,271,151
[45] Jun. 2, 1981

[54] PROTEIN-BOUND POLYSACCHARIDES

[75] Inventors: Tetsuya Hotta, Tokyo; Satoru Enomoto, Fujisawa; Chikao Yoshikumi, Kunitachi; Minoru Ohara, Tokyo; Saburo Ueno, Ichigayadai, all of Japan

[73] Assignee: Kureha Kagaku Kogyo Kabushiki Kaisha, Tokyo, Japan

[21] Appl. No.: 121,142

[22] Filed: Feb. 13, 1980

Related U.S. Application Data

[60] Division of Ser. No. 40,105, May 18, 1979, which is a continuation-in-part of Ser. No. 755,142, Dec. 29, 1976, abandoned.

[30] Foreign Application Priority Data

Jan. 1, 1976 [JP] Japan ..................... 51-318

[51] Int. Cl.³ .................. A23J 1/00; A61K 31/71; A61K 31/73; A61K 37/02
[52] U.S. Cl. ................. 424/177; 260/112 R; 424/180; 424/181; 424/195
[58] Field of Search ............... 424/177, 181, 180, 195; 260/112 R

[56] References Cited

U.S. PATENT DOCUMENTS

| | | | |
|---|---|---|---|
| 3,472,831 | 10/1969 | Vester et al. | 260/112 R |
| 3,759,896 | 9/1973 | Komatsu et al. | 536/1 |
| 3,810,819 | 5/1974 | Okamoto et al. | 260/112 R X |
| 3,856,775 | 12/1974 | Fukuoka et al. | 536/1 |
| 4,051,314 | 9/1977 | Ohtsuka et al. | 536/1 |

FOREIGN PATENT DOCUMENTS

| | | |
|---|---|---|
| 2043971 | 9/1971 | Fed. Rep. of Germany . |
| 2659808 | 7/1977 | Fed. Rep. of Germany . |
| 2070133 | of 1971 | France . |
| 38-1647 | of 1963 | Japan . |
| 1331513 | 9/1973 | United Kingdom . |

OTHER PUBLICATIONS

Nature, Chihara et al., vol. 225, p. 943 (1970).
Proc. of 8th Int. Congress of Chemotherapy=Progress in Chemotherapy, vol. 3, 1973, pp. 799–803, Tsukagoshi et al.
Host Defense against Cancer and its Potentiation, D. Mizuno et al.
(EDS.), Univ. of Tokyo Press, Tokyo/Univ. Park Press, Baltimore, pp. 365–377 (1975).
Carbohydrate Research, 56 (1977), pp. 351–355, Inoue et al.
Chemical Abstracts, vol. 84, 54002e (1976).
Chemical Abstracts, vol. 81, 150305q (1974).
Chemical Abstracts, vol. 80, 91256d (1974).

Primary Examiner—Howard E. Schain
Attorney, Agent, or Firm—Wegner & Bretschneider

[57] ABSTRACT

Disclosed in this invention are protein-bound polysaccharides having antitumor activities. The polysaccharides have molecular weight within a specified range and present a pattern of color reaction peculiar to the saccharides as well as a pattern of color reaction characteristic of amino acids and peptide bonds. The proton nuclear magnetic resonance spectra of the polysaccharides show peculiar absorption bands. The ratio of the polysaccharide portion to protein portion in the polysaccharides is within a specified range. The protein-bound polysaccharides can be obtained by extraction of the mycelia and/or fruit bodies of fungi belonging to Coriolus of Polyporaceae of Basidiomycetes.

12 Claims, 6 Drawing Figures

PROTEIN-BOUND POLYSACCHARIDES

This is a Division of application Ser. No. 40,105 filed May 18, 1979, which in turn is a continuation-in-part of U.S. Ser. No. 755,142, filed Dec. 29, 1976, now abandoned.

FIELD OF THE INVENTION

This invention relates to the novel protein-bound polysaccharide substances having the antitumor activities.

BACKGROUND OF THE INVENTION

Reports have been made on obtainment of the antitumor substances from various kinds of Basidiomycetes in recent years. These substances have a polysaccharide structure and show a significant antitumor or anti-cancer effect in intraperitoneal administrations, but they prove to be extremely low in antitumor activities when administered orally. Therefore, although these substances could be of much interest for scientific studies, their practical utility is scarce.

It is also known that the extracts obtained by extracting fungi belonging to the Coriolus with an aqueous solvent are predominantly composed of protein-bound polysaccharides. However, as these extracts are obtained from native Basidiomycetes and contain complicated compounds composed of various kinds of protein-bound polysaccharides, no definite elucidation has yet been made on the characters of the active antitumor ingredients of these extracts.

SUMMARY OF THE INVENTION

In the course of our studies on the extracts from various kinds of Basidiomycetes with an aqueous solvent, we found that the extracts obtained from the fungi (mycelia and/or fruit bodies) belonging to the Coriolus have an excellent antitumor activity in not only intraperitoneal administrations but also oral administrations. Our further studies on these extracts have led us to successful obtainment of the active ingredient having the antitumor activity from the following process: firstly, an extracted solution was prepared by extracting the fungi with an aqueous solvent, removing the extraction residue from the obtained extract and concentrating the extract. The thus obtained aqueous solution was subjected to a treatment such as salting out with ammonium sulfate or ultrafiltration to get rid of the low molecular weight substances contained therein, then this refined solution was further added with a determined amount of ammonium sulfate for salting out and the formed precipitate was collected; the collected precipitate was dissolved with water and the resultant solution was desalted by dialysis; and then the obtained solution was passed through a DEAE (Diethyl aminoethyl) cellulose column, and the thus adsorbed substance on the column was then eluted out with an aqueous solution of sodium chloride (saline) and the obtained elutant was further added with a determined amount of ammonium sulfate for salting out; the thus formed precipitate was collected and then again dialyzed for desalting. We also succeeded in elucidating the characteristic properties of the active ingredient and attained this invention on the basis of these findings.

Thus, the primary object of this invention is to provide novel protein-bound polysaccharide substances which show excellent antitumor activity even in oral administrations. The other objects of this invention will become apparent from the following detailed description of the invention.

The polysaccharide of the present invention is surprisingly taken into the digestive system without being degraded by the action of intestinal enzymes, such as amylase. In vitro testing has demonstrated this surprising resistance to degradation by intestinal enzymes, thus making the polysaccharide suitable for oral administration.

The polysaccharide of the present invention is contemplated for use against a wide variety of mammalian cancers, including mammary cancer, gastro-intestinal cancers such as cancer of the esophagus, stomach and large colon, lung cancer and brain tumors. The polysaccharide of the invention may, in addition to the oral route mentioned above, be delivered to the patient intraperitoneally, subcutaneously, or intravenously. The dosage will vary dependent upon the mode of administration, with oral dosage for an adult human subject contemplated at from about 300 mg to about 10,000 mg per day with a lesser amount contemplated for intraperitoneal administration.

BRIEF EXPLANATION OF THE DRAWINGS

In the accompanying drawings:

FIGS. 2-1, 2-2, 2-3 and 2-4 show the proton nuclear magnetic resonance spectra of the above substances of this invention.

DETAILED DESCRIPTION OF THE INVENTION

The protein-bound polysaccharide substances (hereinafter referred to simply as present substance) according to the present invention are of a structure in which protein is bonded to a polysaccharide portion. The present substance is odorless, tasteless and water soluble, having light brown or brown color. Also, the present substance has no definite melting point and is gradually blackened and decomposed at a temperature of higher than around 120° C.

Now the characteristic properties of the present substance are described in due order.

PHYSICAL AND CHEMICAL PROPERTIES (1) Color reactions

Color reaction tests were conducted on the aqueous solutions of the present substance to obtain the results shown in Table 1 below.

TABLE 1

| Color reaction | Color | Results |
| --- | --- | --- |
| α-naphtol-sulfuric acid reaction (molish reaction) | Purple | Saccharides |
| Indole-sulfuric acid reaction (Dische reaction) | Brown | Saccharides |
| Anthrone-sulfuric acid reaction | Greenish blue | Saccharides |
| Phenol-sulfuric acid reaction | Brown | Saccharides |
| Tryptophane-sulfuric acid reaction | Purplish brown | Saccharides |
| Lowry-Folin process | Blue | Peptide bonds, tyrosine, |

TABLE 1-continued

| Color reaction | Color | Results |
|---|---|---|
| | | tryptophane, cysteine |
| Ninhydrin reaction after hydrochloric acid hydrolysis (6H HCl, 110° C. 20 hr) | Purplish blue | α-amino acids |

It is apparent from the above-shown results of the color reaction tests that the present substance contains saccharides and protein.

(2) Solubility

The present substance is soluble in water and almost insoluble in methanol, pyridine, chloroform, benzene and hexane.

(3) Hygroscopicity

In order to determine hygroscopicity of the present substance, several specimens were placed in each desiccator maintained at respective given humidity as shown in Table 2 below by taking a saturated solution of salts therein, and the moisture content of each specimen was determined by measuring the change of weight with time. The results are shown in Table 2.

TABLE 2

(Change of moisture uptake with time at each relative humidity)

| Time hr) conditions | Moisture content (%) | | | | | | | |
|---|---|---|---|---|---|---|---|---|
| | 1 | 3 | 7 | 24 | 48 | 72 | 96 | 144 |
| 98% RH 20° C. | 10.0 | 12.5 | 16.0 | 22.5 | 25.5 | 27.0 | 27.0 | 27.0 |
| 79% RH 25° C. | 9.0 | 9.5 | 11.7 | 15.0 | 15.5 | 16.0 | 16.6 | 17.0 |
| 52% RH 20° C. | 9.0 | 9.5 | 11.7 | 15.0 | 15.3 | 15.5 | 15.7 | 16.0 |
| 32% RH 16.4° C. | 8.0 | 8.5 | 9.0 | 10.0 | 12.5 | 12.5 | 12.5 | 12.5 |

Note:
Saturated solution used.
at 32% RH, a saturated solution of sodium chloride-potassium nitrate,
at 52% RH, a saturated solution of sodium bichromate,
at 79% RH, a saturated solution of ammonium chloride,
at 98% RH, a saturated solution of lead nitrate.

As understood from Table 2, each specimen of the present substance suffered little change of appearance, and there were seen no phenomena such as deliquescence which is caused by moisture abosrption.

(4) pH value

The pH value of the present substance was measured by dissolving 1 gr. of specimen in 100 ml of water. It was found that it has pH value within the range of 6.6 to 7.2. This indicates that the present substance is substantially neutral.

(5) Optical rotation

Optical rotation of the present substance was measured by using a 0.25% aqueous solution of specimen to determine the specific rotation $[\alpha]_D^{25}$. It was within the range of 0 to 30, and it is assumed that the present substance was predominantly composed of β-glucan whose specific rotation is in the neighborhood of 0.

(6) Infrared absorption spectrum

Figure 1:
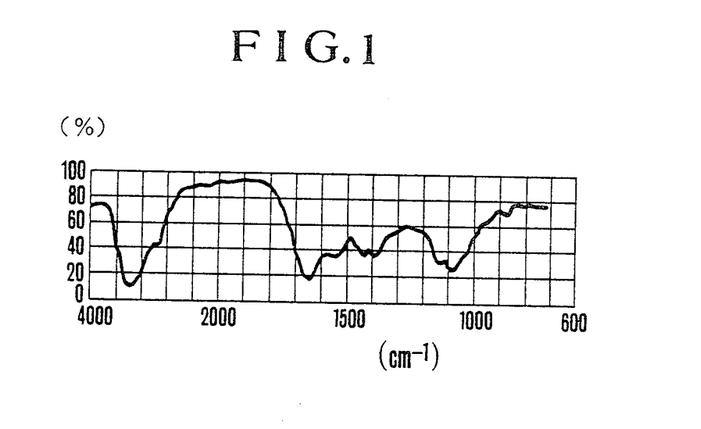
FIG. 1 is a graphic representation of the infrared absorption spectrum of the protein-bound polysaccharide substances according to this invention.

An infrared absorption spectrum of the present substance as measured according to the potassium bromide disk method is shown in FIG. 1 of the accompanying drawings. The broad absorption band at 3600 to 3200 cm$^{-1}$ as noted in FIG. 1 is considered attributable to $v$OH's which are hydrogen-bonded at various degrees. This can be assumed, for example, from the fact that such broad absorption band diminishes or vanishes when the hydroxy groups in the polysaccharide portion of specimen are methoxylated. Absorptions at 1600 cm$^{-1}$ and 1530 cm$^{-1}$ are considered ascribable to deformation vibration of —NH$_2$ and —NH$_1$ respectively, and it is recognized that such phenomenon originates from the protein portion in the specimen. On the other hand, the broad absorption bands at 1200 to 1000 cm$^{-1}$ are considered due to antisymmetric stretching vibration of C—O—C linkage in the pyranose rings in the polysaccharide portion. Also, a characteristic pattern of absorption resulting from β-linkage of glucose in the polysaccharide portion is observed at 890 cm$^{-1}$, but there is hardly seen characteristic absorption resulting from α-linkage at 840 cm$^{-1}$.

STRUCTURAL CHARACTERISTICS (1) Structure of polysaccharide portion

In order to determine the structural characteristics of the polysaccharide portion of the present substance, 10 mg of specimen was added with 3% hydrochloric acid-methanol to perform methanolysis at 100° C. for 16 hours and then, after trimethylsilation according to a ordinary method, subjected to a gas chromatographic analysis. The results showed that glucose accounts for more than 99% of the total saccharides, and other saccharide components such as mannose, galactose, xylose and fucose are very scanty. In order to ascertain the type of glucose (D type or L type), glucose crystals were separated from the hydrolyzates of the present substance. It was found that the melting point of the separated glucose is within the range of 143° to 145° C., and when the glucose crystals were mixed with a standard D-glucose, no depression of melting point was observed. Therefore, the glucose composing the polysaccharide portion of the present substance was identified as D-glucose.

(2) CHARACTERISTICS OF MODE OF LINKAGE OF saccharides constituting the polysaccharide portion.

The position of glycosidic linkage was determined in the following way. The linkage patterns of $G^1 \rightarrow (G^1 \rightarrow$ means glucose structure skeleton), $$\rightarrow ^4G^1 \rightarrow, \rightarrow ^4G_3^1 \rightarrow, \rightarrow ^4G_6^1 \rightarrow, \rightarrow ^3G^1 \rightarrow, \text{ and } \rightarrow ^3G^1 \rightarrow,$$
$$\uparrow \qquad \uparrow \qquad \qquad \uparrow$$

were confirmed from analysis of the monosaccharides obtained according to the periodate oxidation method or Smith's decomposition method, and their constitution ratios were determined by the methylation experiments according to Haworth's method. As for identification, the saccharides obtained from hydrolysis of the methylated compounds were identified by gas chromatography as alditol-acetate and methylglucoside, and further, the individual hydrolyzates were isolated by column liquid chromatography and then crystallized or led into crystalline derivatives thereof for confirmation. The molar ratios of the respective linkage in the present substance are shown in Table 3 below by indexing the molar ratio of G$^1$ linkage as 1. The molar ratios in Table 3 were determined from the area ratios on the gas chromatograph of alditol-acetate.

TABLE 3

| Hydrolyzates of methylated sugars | Linkage | Molar ratio |
|---|---|---|
| 2,3,4,6-tetra-O-methyl-G | $G^1 \rightarrow$ | 1 |
| 2,3,6-tri-O-methyl-G | $\rightarrow ^4G^1 \rightarrow$ | 3–12 |
| 2,3-di-O-methyl-G | $\rightarrow ^4G_6^1 \rightarrow$ | 0.5–3 |

TABLE 3-continued

| Hydrolyzates of methylated sugars | Linkage | Molar ratio |
|---|---|---|
| 2,6-di-O-methyl-G | →⁴G₃¹→ (with ↑ above and below) | 0.1–2.5 |
| 2,4,6-tri-O-methyl-G | →³G¹→ | 2 or less |
| 2,4-di-O-methyl-G | →³G₆¹→ (with ↑ below) | 2 or less |

As apparent from the above table, it is considered that the polysaccharide portion of the present substance is mostly composed of β-1,4 linkages, but there also exist β-1,3 linkages and many branches in this polysaccharide portion. It may be construed from this that the polysaccharide portion of the present substance is of a structure where side chains are bonded to the main chains of cellulose and β-1,3 linkages exist therein scatteredly.

(3) Characteristics of protein portion

The protein portion of the present substance was hydrolyzed according to a ordinary method, and the amino acids composing the hydrolyzate were analyzed by using an amino acid analyzer. The results are shown in Table 4 below.

TABLE 4

(Amino acids constituting protein portion)

| Kinds of amino acid | Weight (%) |
|---|---|
| Aspartic acid | 13–19 |
| Threonine | 6–10 |
| Serine | 6–11 |
| Glutamic acid | 12–18 |
| Proline | trace–8 |
| Glycine | 6–9 |
| Alanine | 6–13 |
| Cysteine | trace |
| Valine | 5–11 |
| Methionine | 1–4 |
| Isoleucine | 3–5 |
| Leucine | 6–8 |
| Tyrosine | trace–3 |
| Phenylalanine | 3–6 |
| Tryptophane | trace–2 |
| Lysine | 2–4 |
| Histidine | trace–2 |
| Arginine | 2–4 |
| Ammonia | 2–6 |

As noted from the above table, the protein portion of the present substance contains 18 kinds of amino acids, of which the acidic amino acids and neutral amino acids are predominant, and the basic amino acids are very scanty in quantity. It is also characteristic of the present substance that aspartic acid, threonine, serine, glutamic acid, glycine, alanine, valine and leucine put together account for more than 70% of all the kinds of amino acids found in the protein portion.

Although the presence of glucosamine was also confirmed in the amino acid analysis, the quantity of this substance was less than 1% by weight of the total amount of protein.

As for linkage of these amino acids to the polysaccharide portion it is assumed that the amino acids are tightly bound in the form of the oligopeptide or peptide to the polysaccharide portion. This assumption can be derived from the results of various kinds of tests such as mentioned below.

Firstly, when tested according to Sevag's method which is often used for removing protein mixed in the specimen, the specimens of the present substance produced no precipitate. This method is practiced by adding 1/5 volume of chloroform and 1/25 volume of n-butanol to the aqueous solution of each specimen (it is desirable to adjust pH of the solution at 4 to 5) and then shaking thoroughly the mixture, and the solution is carefully observed whether there is produced any gel-like precipitate or not. If the polysaccharide portion and protein in the specimen exist in the form of a mere mixture, protein is denatured and gelled to precipitate between the water layer and the chloroform layer, but no such precipitation occurs in case the polysaccharide and protein are bound.

In another precipitation test conducted similarly by using trifluorotrichloroethane, there was here again witnessed no formation of precipitates of the specimens of the present substance.

Also, the specimens of the present substance showed no change of protein content in the test in which protease, a proteolytic enzyme, was acted to the specimens.

Judging from the results of various kinds of tests such as above-mentioned, it is supposed that, in the substance of this invention, the polysaccharide and protein portions are not merely mixed forms each other but are bound chemically to each other.

As regards the mode of linkage of the polysaccharide portion and protein portion in the present substance, there are generally known the following types of sugar and protein linkage: N-acylglycosilamine type linkage, O-glycoside type linkage and glycosideester type linkage, but in the case of the present substance, in view of the facts that the linkages can hardly be broken with weak alkali and that the presence of glucosamine is noticed in an amino acid analysis after hydrolysis of the present substance, it is considered that N-acylglycosilamine type linkage are predominant in the present substance. (4) Proton nuclear magnetic resonance spectra (N.M.R.)

N.M.R. (100 MHz) of the present substance was measured by using heavy water as solvent and adopting sodium 2,2-dimethyl-2-silanopentane-5-sulfonate (D.S.S.) as internal standard. The results are shown in FIG. 2. In FIG. 2, if it is assumed that absorption at 0.5 to 2.5 ppm under the D.S.S. standard is attributable to side chain protons of the protein portion and that absorption at 2.5 to 6.0 ppm is attributable to protons of the polysaccharide portion, and if the properties of the present substance under the above-stated definitions is expressed by way of proton strength ratio between the two, it is noted that such ratio is within the range of 95/5 to 55/45. In the above measurements of N.M.R., in order to eliminate the influence of residual light water in heavy water, there were used the values after correction under the supposition of the Lorenz's curve.

Figure 3:
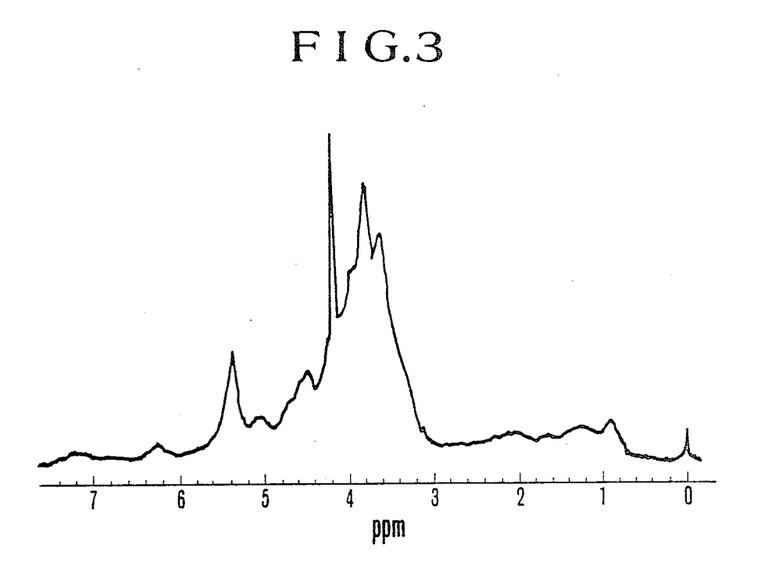
FIG. 3 shows the proton nuclear magnetic resonance spectrum of PS-K treated as control.
Figure 21:
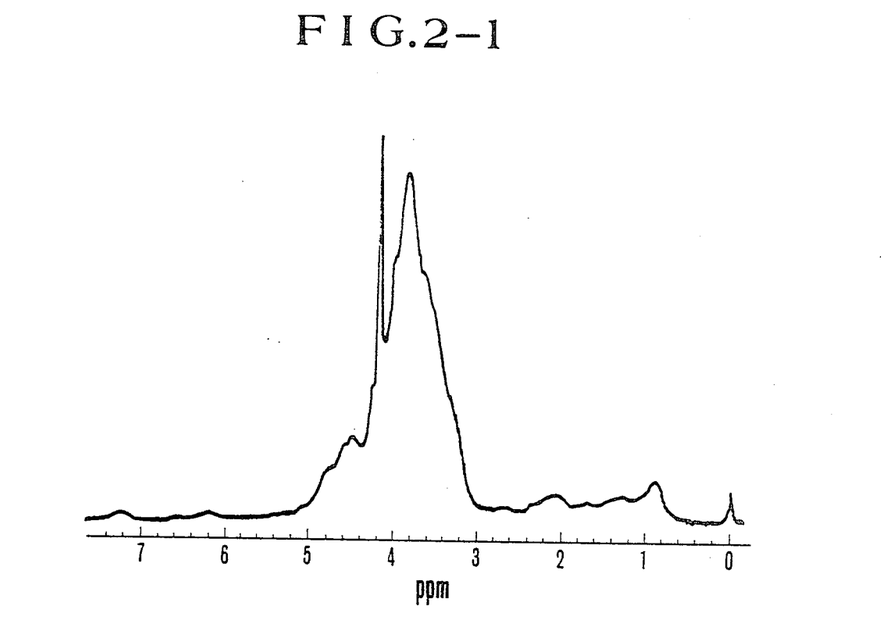
Figure 22:
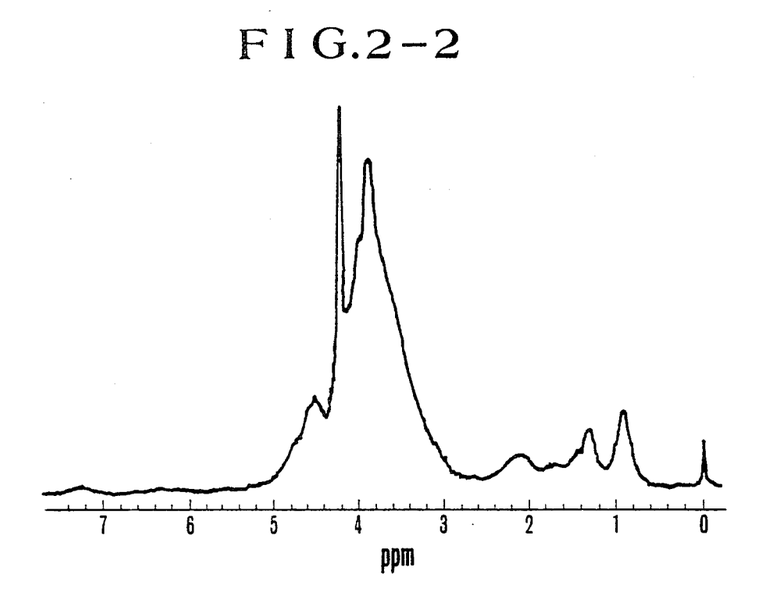
Figure 23:
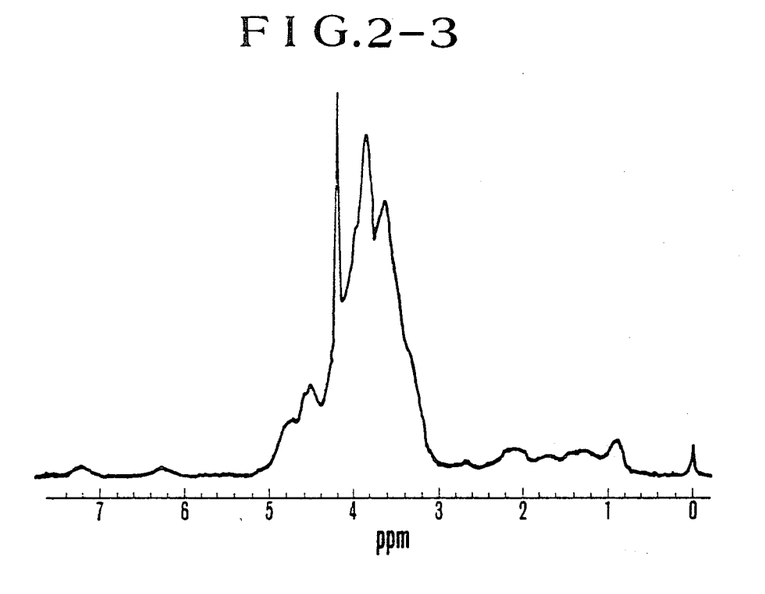
Figure 24:
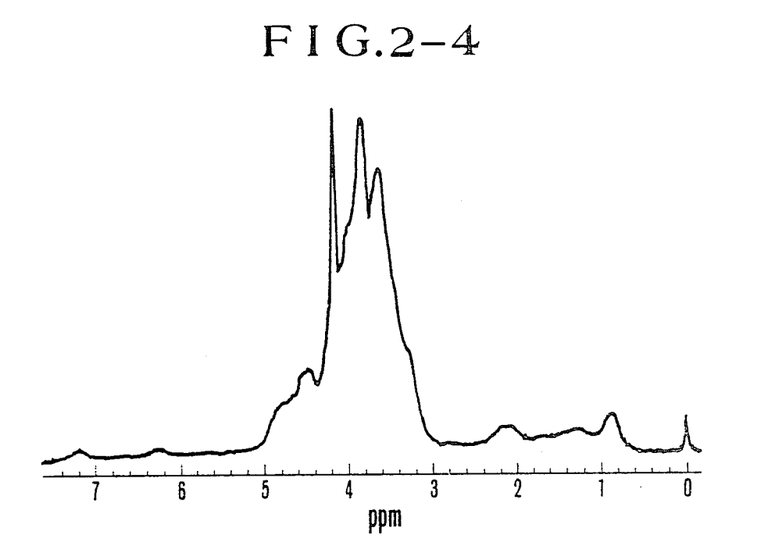

In absorption of the polysaccharide portion, the prominent rise of absorption at 2.5 to 4.1 ppm is due to the methylene protons at 2- to 6-positions in the pyranose rings in the sugar chain. For reference, there is shown in FIG. 3 the N.M.R. spectra of a product obtained from an extract of the fungi belonging to Coriolus versicolor (Fr.) Quèl. (Polystictus versicolor Fr.) by subjecting the extract to filtration under pressure, heat sterilization and spray drying. (Such product is reported by the name of PSK, so it is hereinafter referred to as PS-K.) The greatest difference between PS-K and present substance as noticed from the comparison of FIG. 2 and FIG. 3 is that, in the case of the present substance, there is observed absolutely no absorption in the range of 4.9 to 6.0 ppm originating from α-linkages. This fact endorses that the polysaccharide portion of the present substance is constituted from the β-D-glucan alone.

It is known that, in FIG. 2, absorption at 4.5 ppm is concerned with $\beta$-(1→4) and $\beta$-(1→6) in the methine protons at 1-position while absorption at 4.7 ppm is associated with $\beta$-(1→3) and $\beta$-(1→2) in the methine protons in 1-position, so that it is possible to determine the ratio of $\beta$-(1→4) and $\beta$-(1→6)/$\beta$-(1→3) and $\beta$-(1→2), but since there is also involved the branch structure, the above-stated methylation method must be employed for elucidation of the fine structure.

As regards the protein portion, it is hardly possible to presume the structure of such protein portion only by the measurements of the nuclear magnetic resonance spectra. However, as the present substance shows absorption at certain given regions as mentioned below, this method is considered very favorable for identification of the present substance.

The present substance has the characteristic to show absorption at 0.9±0.1 ppm, 1.2±0.1 ppm, 2.0±0.1 ppm, 4.5±0.1 ppm and 4.7±0.1 ppm, no absorption in the region of 4.9 to 6.0 ppm, and broad absorption in the region of 3.0 to 4.4 ppm.

(5) Molecular weight

The molecular weight of the present substance, as measured by an ultracentrifugal method, was within the range of 5,000 to 300,000, and the average molecular weight was within the range of 10,000 to 100,000. The values obtained according to the other measuring methods, such as fractionating by the ultra-filtration, also pointed to the range of 10,000 to 100,000. Therefore, it may be supposed that the average molecular weight of the present substance is within the range of 10,000 to 100,000.

It was thus ascertained that the present substance is a novel substance obtained from the protein-bound polysaccharides (PS-K) originating from fungi belonging to the Coriolus and not containing $\alpha$-glucan as measured by N.M.R., therefore, the present substance should be distinguished from PSK. It is easy to identify the substance by specifying the absorption region by N.M.R. measurements, and in this respect, we believe that the identification techniques relating to the substance of this invention will prove to be a precious guide for the study of complicated high molecular substances derived from natural materials.

As the present substance is obtained by separating from the mucopolysaccharide substances (PS-K), it is quite natural that it should have a high antitumor activity, and such activity can be obtained even if the substance is administered orally.

We will now describe the antitumor activity of the present substance by showing the results of various kinds of animal tests.

Acute toxicity:

Acute toxicity in mice and rats

The mice used in this test were of ICR-JCL s-rain, 4 to 5 weeks old, weighing 21 to 25 gr., and the rats were of Donryu strain, 4 to 5 weeks old, weighing 100 to 150 gr. The substance of this invention was administered through the following four routes: intravenous, subcutaneous, intraperitoneal and oral. Observations were made on general symptoms, death and body weight through the period of 7 days after administration of the substance, and after completion of this observation period, the animals were killed and autopsied. The results are shown in Table 5 below. No death was caused by administration of the substance even with the maximum dosage in both rats and mice, and it was practically impossible to calculate the numerical values for $LD_{50}$.

TABLE 5

| Kind of animal | Route of administration | Acute toxicity in mice and rats $LD_{50}$ (mg/kg) | |
|---|---|---|---|
| | | Female | Male |
| Mice | Intravenous | >1,300 | >1,300 |
| | Subcutaneous | >5,000 | >5,000 |
| | Intraperitoneal | >5,000 | >5,000 |
| | Oral | >20,000 | >20,000 |
| Rats | Intravenous | >600 | >600 |
| | Subcutaneous | >5,000 | >5,000 |
| | Intraperitoneal | >5,000 | >5,000 |
| | Oral | >20,000 | >20,000 |

Antitumor activity tests (1) In vitro antitumor activity (1)-1 In vitro inhibitory activity against growth of ascites hepatoma AH-13 cells 50% growth inhibitory concentration $IC_{50}$ was examined. The substance of this invention, diluted stepwise, was added to a suspension of ascites hepatoma AH-13 cells, and after 48-hour culture, the living cells were counted by a staining method to determine growth inhibition. The result revealed that $IC_{50}$ of the present substance was 100 μg/ml.

(1)-2 In vitro activity against growth of Ehrlich ascites cells of mice

The influence of the substance of this invention on uptake of $^3H$-uridine and $^3H$-thymidine by Ehrlich ascites cells of mice (hereinafter shortened as EC cells) were examined. EC cells ($5 \times 10^5$/ml) were incubated in Eagle MEM culture media containing 500, 1,000 and 2,000 μg/ml of the substance of this invention and 0.5 Ci/ml of $^3H$-uridine or $^3H$-thymidine at 37° C. for 120 minutes. As control, sterile physiological saline was added in place of the substance of this invention. As a result, the substance of this invention could reduce the uptake of $^3H$-uridine into RNA of EC cells to about 70% of the control at 500 μg/ml of the substance of this invention after 120 minutes, to about 65% of the control at 1,000 μg/ml, and to about 60% of the control at 2,000 μg/ml. It could also reduce the uptake of $^3H$-thymidine into DNA of EC cells to about 65% at 500 μg/ml, about 60% at 1,000 μg/ml and about 50% at 2,000 μg/ml, after 120 minutes, respectively.

(2) In vitro and in vivo antitumor activity test (Suppression activity of the substance of this invention against growth of Ehrlich ascites cells).

The suppression activity of the substance of this invention against growth of Ehrlich ascites cells of mice (hereinafter shortened as EC cells) was investigated. The EC cells ($5 \times 10^6$ cells/ml) were incubated in a Hanks' solution containing 5,000 μg/ml of the substance of this invention at 37° C. for 3 hours, and after incubation, EC cells were inoculated into the peritoneal cavities of JCR-JCL female mice (10 mice in each group) at the rate of $10^6$ cells per mouse and the deaths were examined during the period of 20 days.

As a result, no death was seen during the period of 20 days after inoculation in the mice to which EC cells treated with the substance of this invention has been inoculated. There were some mice who had no accumulation of abdominal dropsy. On the other hand, all of the mice of the group inoculated with the control EC cells died of tumor during the 20-day period after inoculation.

(3) In vivo antitumor activity tests

The results of the in vivo antitumor activity tests on mice and rats are as shown in Table 6 below. The substance of this invention revealed high antitumor activity in each case.

moved. The resultant solution is again added with ammonium sulfate in an amount corresponding to 40% of its saturation value and the produced precipitate is collected. The collected precipitate is dissolved with water and then desalted by dialysis. The resultant solution is

TABLE 6

In vivo antitumor activity against inoculated tumor in mice and rats

| Tumor | Mouse or rat strain | Inoculation & administration route | Nos. of cells inoculated per animal | Time till start of administration after inoculation | Dose (mg/kg. day × nos. of times of administration) | Time required for evaluation effect (days after inoculation) | Tumor inhibition ratio (%) |
|---|---|---|---|---|---|---|---|
| Sarcoma-180 (solid type) | ICR-JCL | SC - iP | $10^6$ | 24 hr. | 500 × 10 | 32 | 97–100 |
|  |  | SC - iP | $10^6$ | 24 | 250 × 10 | 32 | 97–100 |
|  |  | SC - PO | $10^6$ | 24 | 1000 × 10 | 32 | 65–90 |
|  |  | SC - PO | $10^6$ | 24 | 500 × 10 | 32 | 83–89 |
|  |  | SC - iP | $10^6$ | 24 | 10 × 11 | 32 | 97–100 |
| Ehrlich carcinoma (solid type) | ICR-JCL | SC - iP | $10^6$ | 24 | 50 × 10 | 35 | 100 |
| Ascites hepatomas AH-13 | Donryu | iP - iP | $10^6$ | 7 days | 250 × 10 | 60 | More than 70% of subject animals cured and survived |

PREPARATION OF THE PRESENT SUBSTANCE

Now the process for preparation of the substance of the present invention is described. As starting material, it is possible to use not only the specified strains of *Coriolus versicolor* (Fr.) Quél. (*Polystictus versicolor* Fr.)—Fermentation Research Institute of Agency of Industrial Science and Technology Deposit FERM-P No. 2412-2426 (Strain Nos. CM-101-115 Strains)—but also other strains of *Coriolus versicolor* (Fr.) Quél. and strains belonging to other Species such as *Coriolus consors* (Berk.) Imaz. [Irpex consors Berk.], *Coriolus pubescens* (Fr.) Quél. [*Polyporus pubescens* Schum. ex Fr.; *Tyromyces pubescens* (Fr.) Imaz.], *Coriolus biformis* (Klotz.) Pat. [*Polystictus biformis* (Kl.) Fr.], *Coriolus hirsutus* (Fr.) Quél. [*Polystictus hirsutus* Fr.], *Coriolus conchifer* (Schw.) Pat. [*Polystictus conchifer* (Schw.) Sacc.; *Poronidulus conchifer* (Schw.) Murr.], *Coriolus pargamenus* (Fr.) Pat. [*Polystictus pargamenus* Fr.]. However, it is most advantageous for industrial production to use the above-mentioned CM-101 strain as it can provide the highest yield of production of the present substance.

The substance of this invention is contained in the extracts of the fruit bodies and mycelia of Coriolus.

The fungi are precultured and the mycelial mat grown on the surface of culture medium are homogenized with physiological saline to prepare the seeds for production culture. The seeds are subjected to stationary culture or submerged culture to develop the mycelia, which are extracted by using an aqueous solvent such as hot water or dilute alkaline solution. The obtained extract, after removing the extraction residue therefrom, is concentrated and then subjected to salting out with ammonium sulfate or ultra-filtration to eliminate the low molecular weight substances. The thus refined extract is concentrated up to 5–10% by weight. This concentrated solution is further added with ammonium sulfate in an amount corresponding to 25% of its saturation value for the purpose of conducting fractional precipitation, and the formed precipitate is removed. The resultant solution is again added with ammonium sulfate in an amount corresponding to 40% of its saturation value to form a precipitate, and the formed precipitate is again dissolved with water and then desalted by dialysis. The resultant refined product is dried to obtain the object substance of this invention.

A reviewed above, the protein-bound polysaccharide substance according to this invention shows a very excellent effect when used as an orally administered antitumor agent. The present substance also gives immunopotentiation through the host and is effective for preventing or minimizing decline of immunity or physical strength of the patients who have undergone various kinds of treatments such as chemotherapy, radiotherapy, surgical operation or blood transfusion no matter whether they are affected by cancer or not. Furthermore, the present substance is also effective for protecting the patients against infectious diseases such as hepatitis or pneumonia which may be caused by infection of virus or bacteria as a result of loss or decline of immunity or physical strength.

Also, the substance of this invention, when orally administered to the patient, not only bring about improvements of the general physical conditions but also work marvelously in expediting the intestinal activity and promoting appetite of the patient. The present substance also proves extremely helpful in promoting the bowel's action of a patient who is bed ridden for a long time.

The present invention is now described in further detail by way of some preferred embodiments thereof.

EXAMPLES 1-4

Each strain of CM-101 (Fermentation Research Institute of Agency of Industrial Science and Technology Deposit FERM-P. No. 2412), CM-102 (FERM-P. No. 2413) and CM-103 (FERM-P. No. 2414) belonging to Coriolus versicolor (Fr.) Quel. (*Polystictus versicolor*

Fr.), was inoculated in a 200 ml erlenmeyer flask containing 30 ml of a culture medium having the following compositions: 5% glucose, 0.2% peptone, 0.3% yiest extract, 0.1% $KH_2PO_4$ and 0.1% $MgSO_4.7H_2O$, and cultured stationally at 25° to 27° C. for 10 days, and the mycelial mat grown on the surface of culture medium were homogenized with physiological saline to thereby prepare the seeds. The seeds were then inoculated in each of the 1.0 liter culture flasks containing 200 ml of the same culture medium and incubated at 25° to 27° C. for 25 days to thereby obtain the mycelia. The mycelial yield was 4 to 4.3 gr. per flask for CM-101, 2.0 to 2.5 gr. for CM-102, and 2.7 to 3.2 gr. for CM-103.

Then, 3 liters of distilled water was added to each of 100 gr. of the prepared mycelia, and each of the mycelia was extracted under agitation at 98° C. for 3 hours. After completion of extraction, each of the solution was separated into extract and extraction residue, and the extraction residue was further subjected to the same extraction treatment as mentioned above by using each aqueous solvent shown in Table 7 below. Each of extracts was collected and then subjected to concentration. The concentrated solution of the extract was saturated with ammonium sulfate to form a precipitate. The obtained precipitate was again dissolved in water and subjected to desalting by dialysis using a cellulose membrance. Thus obtained solution was concentrated up to 5% by weight, then added with ammonium sulfate in an amount corresponding to 25% of its saturation value. After removing the precipitate formed by the treatment mentioned above, the solution was again added with ammonium sulfate in an amount corresponding to 40% of its saturation value, and the obtained precipitate was dissolved with water and further subjected to same desalting as mentioned above, then passed through a DEAE-cellulose column, and the adsorbed substance on the column was washed with water, then eluted with 1 mole saline. The elutant was again added with ammonium sulfate in an amount corresponding to 40% of its saturation value, and the resultantly formed precipitate was collected and dissolved again with water. The obtained solution was desalted by dialysis, and concentrated, then spray-dried to thereby obtain the object substance. The properties of the obtained substance and the results of animal tests thereof are shown in Table 7. The "alkali extraction method" using alkali as solvent, shown in Table 7 was same as the above-described process except that a 1/10 N caustic soda solution was used instead of water in reextraction of the residue and pH was adjusted to the reatral value with 1/10 N hydrochloric acid after completion of extraction.

In Table 7, the infrared absorption spectrum measured according to the potassium bromide disk method was as diagrammatically represented in FIG. 1, that is, there were seen absorption of $\nu OH$ at 2600-3200 $cm^{-1}$, deformation vibrations of $-NH_2$ and $-NH$ at 1600 $cm^{-1}$ and at 1530 $cm^{-1}$, respectively, broad absorption at 1200-1000 $cm^{-1}$, antisymmetric stretching vibration of pyranose rings in the polysaccharide portion of C—O—C linkage, and peculiar absorption at 890 $cm^{-1}$ due to $\beta$-linkage of glucose, but absorption ($\alpha$-linkage) at 840 $cm^{-1}$ was scarcely seen.

As there was noticed no much difference among the respective specimens concerning the infrared absorption spectrum, the results of Example 1 alone were shown representatively.

The measurements of NMR were conducted by adopting DSS as internal standard and using heavy water as solvent. Shown in the Table 7 are the values after correction under the supposition Lorenz's curve for eliminating the influence of residual light water in heavy water.

The molecular weights of the present substance were measured by using the ultracentrifugal method. They were within the range of 5000 to 300,000 in all the spcimens. For measurements, there were employed the sedimentation equilibrium and synthetic boundary pattern using an interference optical system. The experiment conditions were as follows: specimen concentration, 0.3%; solvent, 1/10 M KCl; temperature, 25° C.; length of solution column, 1.7 mm; speed, 22,000 r.p.m.; measuring time, 5 hours.

The amino acid analysis was performed according to a ordinary method by adding 4 ml of 6 N hydrochloric acid to 10 mg of each specimen, freezing it with dry ice acetone, sealing same in a tube under reduced pressure, hydrolyzing at 110° C. for 24 hours, drying and then dissolving in 30 to 40 ml of a citric acid buffer solution with pH of 2.20.

For determining the specific rotation, first the optical rotation was measured with D line (589 m$\mu$) of sodium by using 0.25% aqueous solution of each specimen and 5 cm cells and the specific rotation $[\alpha]_D^{25}$ was calculated from the measured optical rotation $\alpha$.

The measurement of the monosaccharides composition of the present substance was made in the following way. 3 mg of each specimen was put into a 5 mm glass ampule, to which was added 10 ml of 3% hydrogen chloride methanol to perform methanolysis at 100° C. for 16 hours, the resultant product was neutralized with silver carbonate and filtered at room temperature. The filtrate was evaporated to dryness and then dissolved in 0.5 ml of dry pyridine. The obtained solution was added with 0.2 ml of hexamethyldisilazane and 0.3 ml of trimethylchlorosilane, and the mixture was allowed to stand at room temperature for 30 minutes, to perform trimethylsilation. Upon completion thereof, the mixture was dissolved in chloroform, and after removing the excess reagent by washing with water, the obtained solution was evaporated to dryness. The thus treated substance (trimethylsilate) was dissolved in carbon tetrachloride and measured by gas chromatograph.

The mode of linkage of saccharides was determined according to Haworth's method. That is, 2 gr. of each specimen was dissolved in 10 ml of 1 N NaOH solution and, while maintaining the mixture at 40° to 50° C. in a nitrogen stream, under violent agitation, 20 ml of dimethylsulfuric acid and 40 ml of 30% sodium hydroxide solution were added dropwise over a period of several hours, and after allowing the mixture to stand overnight, it was subjected to the same treatment with the same amount of methylating reagent. The reaction solution, after neutralized, was dialyzed in running water and the dialyzate was concentrated under reduced pressure and subjected to the methylation three times, and after additional neutralization and dialysis, the mixture was evaporated to dryness under reduced pressure. The residual substance was dissolved in 20 ml of chloroform-methanol (10:1) mixed solution, to which was added petroleum ether-ether (1:1) mixed solution to precipitate the methylated substance. Then, about 20 mg of this methylated substance was hydrolyzed with 1 N sulfuric acid at 100° C. for 16 hours, and the hydrolyzate was led into alditol-acetate according to an ordinary method and the molar ratio was determined from the peak area on the gas chromatograph. In order to distinguish between 2,3,6-Tri-O-Me-G and 2,3,4-Tri-O-Me-G, 20 mg of the methylated substance was subjected to methanolysis at 100° C. for 16 hours in a sealed tube by using 3% hydrogen chloride methanol. The presence of 2,3,4-Tri-O-Me-G was not confirmed in the gas chromatographic analysis of the methanolysis product. Each of the above decomposed products was identified on the gas chromatograph by using standard. Also, each of the above-mentioned decomposed products was isolated by using column liquid chromatography and either crystallized or led into a crystalline derivative.

The properties, structural characteristics and antitumor activites of the thus obtained protein-bound polysaccharide substances are shown comprehensively in Table 7.

TABLE 7

| Example No. | 1 | 2 | 3 | 4 |
|---|---|---|---|---|
| Deposit No. FERM-P | No. 2412 | No. 2412 | No. 2413 | No. 2414 |
| Strain No. | CM 101 | CM 101 | CM 102 | CM 103 |
| Extraction method | Hot water | Alkali | Hot water | Alkali |
| Yield (g) per 100 g of dry fungi | 0.7 | 0.9 | 0.3 | 0.4 |
| Molecular weight ($\times 10^4$) | 0.8–25 | 0.5–28 | 1.0–19 | 0.8–29 |
| Average mol. wt. ($\times 10^4$) | 6.8 | 9.0 | 4.7 | 8.9 |
| Color reaction (saccharide) | | | | |
| α-naphtol-sulfuric acid reaction | Purple | Same as left | Same as left | Same as left |
| Indol-sulf. acid reaction | Brown | Same as left | Same as left | Same as left |
| Anthrone-sulf. acid reaction | Greenish blue | Same as left | Same as left | Same as left |
| Phenol-sulf. acid reaction | Brown | Same as left | Same as left | Same as left |
| Tryptophane-sulfuric acid reaction | Purplish brown | Same as left | Same as left | Same as left |
| Color reaction (protein) | | | | |
| Lowry-Folin method | Blue | Same as left | Same as left | Same as left |
| Ninhydrin reaction after hydrochloric acid hydrolysis (6N—HCl, 20 hr.) | Purplish blue | Same as left | Same as left | Same as left |
| Specific rotation $[\alpha]_D^{25}$ | 0 | +2 | +1 | 0 |
| Infrared absorption spectra | | | | |
| 3600–3200 cm$^{-1}$ | Present | Present | Present | Present |
| 1600 cm$^{-1}$ | " | " | " | " |
| 1530 cm$^{-1}$ | " | " | " | " |
| 1200–1000 cm$^{-1}$ | " | " | " | " |
| 890 cm$^{-1}$ | " | " | " | " |
| 840 cm$^{-1}$ | Absent | Absent | Absent | Absent |
| NMR spectra (drawing) | FIG. 2-1 | FIG. 2-2 | FIG. 2-3 | FIG. 2-4 |
| Absorption region (ppm) | | | | |
| 0.9 ± 0.1 | Present | Present | Present | Present |
| 1.2 ± 0.1 | " | " | " | " |
| 2.0 ± 0.1 | " | " | " | " |
| 4.5 ± 0.1 | " | " | " | " |
| 4.7 ± 0.1 | " | " | " | " |
| 5.0 ± 0.1 | Absent | Absent | Absent | Absent |
| 5.4 ± 0.4 | " | " | " | " |
| 3.0 ± 4.4 | Present | Present | Present | Present |
| Absorption intensity ratio | | | | |
| Polysaccharide | 86.1 | 79.8 | 86.2 | 85.5 |
| Protein | 13.9 | 20.2 | 13.8 | 14.5 |
| Glycosidic analysis (mode of linkage) | | | | |
| →$^1$G$^4$→ | 5.3 | 3.5 | 8.0 | 7.0 |
| →$^1$G$^3$→ | 0.7 | 0.1 | 2.9 | 0.7 |
| →$^1$G$_6^4$→ | 0.8 | 0.9 | 2.0 | 1.3 |
| →$^1$G$_3^4$→ ↑ | 2.0 | 0.3 | 1.0 | 0.2 |
| →$^1$G$_6^3$→ ↑ | 0.3 | trace | 0.2 | 0.4 |
| $^1$G→ ↑ | 1 | 1 | 1 | 1 |
| Composing monosaccharide | Glucose | Glucose | Glucose | Glucose |
| Proportion (%) | Over 99 | Over 99 | Over 99 | Over 99 |
| Amino acid analysis | | | | |
| Aspartic acid | 18.4 | 14.8 | 13.5 | 14.6 |
| Threonine | 7.1 | 8.1 | 7.3 | 9.2 |
| Serine | 6.4 | 6.4 | 7.0 | 7.2 |
| Glutamic acid | 12.3 | 14.0 | 14.0 | 13.1 |
| Proline | 1.7 | 3.8 | 1.5 | 1.8 |
| Glycine | 7.6 | 7.4 | 7.8 | 7.1 |
| Alanine | 7.8 | 9.5 | 8.5 | 8.9 |
| Cysteine | + | + | + | + |
| Valine | 7.5 | 7.4 | 7.6 | 7.6 |
| Methionine | 1.4 | 1.5 | 1.7 | 1.7 |

TABLE 7-continued

| Example No. | 1 | 2 | 3 | 4 |
|---|---|---|---|---|
| Isoleucine | 4.6 | 4.3 | 4.7 | 4.7 |
| Leucine | 8.0 | 7.1 | 8.0 | 7.9 |
| Tyrosine | 2.2 | 1.8 | 1.8 | 2.0 |
| Phenylalanine | 5.0 | 4.3 | 5.2 | 5.0 |
| Tryptophane | + | + | 0.9 | + |
| Lysine | 2.8 | 2.4 | 2.8 | 2.4 |
| Histidine | 1.5 | 1.4 | 1.7 | 1.5 |
| Arginine | 3.4 | 2.9 | 2.8 | 2.8 |
| (Ammonia) | 2.3 | 2.9 | 3.2 | 2.5 |
| Total of aspartic acid, serine, glutamic acid, glycine, alanine, valine and leucine | 75.1 | 74.7 | 73.7 | 75.6 |
| Acute toxicity (mice) (LD$_{50}$ (mg/kg)) | | | | |
| Intravenous (male) | Over 1300 | Same as left | Same as left | Same as left |
| (female) | Over 1300 | Same as left | Same as left | Same as left |
| Subcutaneous (male) | Over 5000 | Same as left | Same as left | Same as left |
| (female) | Over 5000 | Same as left | Same as left | Same as left |
| Intraperitoneal (male) | Over 5000 | Same as left | Same as left | Same as left |
| (female) | Over 5000 | Same as left | Same as left | Same as left |
| Oral (male) | Over 20000 | Same as left | Same as left | Same as left |
| (female) | Over 20000 | Same as left | Same as left | Same as left |
| Acute toxicity (rats) [LD$_{50}$ (mg/kg)] | | | | |
| Intravenous (male) | Over 600 | Same as left | Same as left | Same as left |
| (female) | Over 600 | Same as left | Same as left | Same as left |
| Subcutaneous (male) | Over 5000 | Same as left | Same as left | Same as left |
| (female) | Over 5000 | Same as left | Same as left | Same as left |
| Intraperitoneal (male) | Over 5000 | Same as left | Same as left | Same as left |
| (female) | Over 5000 | Same as left | Same as left | Same as left |
| Oral (male) | Over 20000 | Same as left | Same as left | Same as left |
| (female) | Over 20000 | Same as left | Same as left | Same as left |
| Antitumor activity | | | | |
| In vitro inhibition against growth of ascites hepatoma AH-13 cells | | | | |
| IC$_{30}$ μg/ml | 105 | 97 | 100 | 98 |
| In vitro inhibitory effect against growth of Ehrlich ascites cells (EC cells) of mice | | | | |
| After 120-minute uptake of $^3$H-uridine into RNA of EC cells (the control is given as 100) | | | | |
| 500 μg/ml | 71 | 70 | 72 | 73 |
| 1000 μg/ml | 64 | 65 | 65 | 63 |
| 2000 μg/ml | 59 | 60 | 60 | 59 |
| After 120-minute uptake of $^3$H-thymidine into DNA of EC cells (the control is given as 100) | | | | |
| 500 μg/ml | 63 | 65 | 64 | 65 |
| 1000 μg/ml | 60 | 61 | 59 | 60 |
| 2000 μg/ml | 50 | 51 | 52 | 51 |
| Suppression against growth of Ehrlich ascites cells | | | | |
| 300 μg/ml | All survived | Same as left | Same as left | Same as left |
| In vivo antitumor activity (growth inhibition) | | | | |
| Mouse sarcoma-180 | | | | |
| iP  10 mg/kg | 98 | 99 | 100 | 99 |
| iP  250 mg/kg | 100 | 100 | 98 | 98 |
| iP  500 mg/kg | 100 | 100 | 100 | 100 |
| PO  500 mg/kg | 85 | 84 | 85 | 86 |
| PO  1000 mg/kg | 90 | 87 | 89 | 90 |
| Mouse Ehrlich | | | | |
| iP  50 mg/kg | 100 | 100 | 100 | 100 |
| Rat AH-13 (survival/number of rats used, after 60 days) | | | | |
| iP  250 mg/kg | 7/10 | 8/10 | 8/10 | 8/10 |

Clinical Results of the Protein-bound Polysaccharides of the Present Invention

Case 1: (Cancer of the breast)

A woman of 49 years suffering from cancer of the breast was treated by the administration of 3 g/day of the present substance divided into 2 equal parts, one part at the morning and the other part in the evening. After 5 weeks of administration, the size of the tumour reduced from 6×5 cm to 4×4 cm showing a clear degeneration. After that she had a radical operation to extirpate the tumour and at the same time, administration of the present substance was begun to be continued for one month. Even today, after 6 months of the operation, she is alive without any recurrence and with a good health state.

Case 2: (Recurrent rectal cancer)

A man of 54 years, although he had a radical operation for rectal cancer, recognized ache and a node on the perineum, and the recurrence was confirmed by exploratory excision. Although mitomycin C and 5-fluorouracil were administered, the aggravation of ache stopped the chemotherapy, and the administration of the present substance was begun at a dose of 3-6 g/day. From 2-3th week, the ache was relieved and the node showed a reduction. At present he is alive at the last mentioned state.

Case 3: (Carcinoma of the lung)

A woman of 68 years was examined by chest roentgenography on her general fatigue and cough, the examination showing tumour-type shadow in the right lower lung field 50×50 mm in size. When the administration of the present substance was begun at a dose of 3 g/day, the tumour reduced a little with size of 50×45 mm after 10 days. After 20 days, when the tumour reduced in size to 40×40 mm she had an excision of the right lower lobe. It was an undifferentiated carcinoma, primary one of the right lower lobe $S_{10}$. A metastasis was recognized on the right hilar lymph node showing that the operation was not a curative one. After that, the administration of the present substance is continuing and no recurrence after the operation is found without any remarkable change.

Case 4: (Carcinoma of the esophagus)

A woman of 58 years showed metastasis on the bones of the chest and the lambar after 7 months of the radical operation of the carcinoma of the lower esophagus and complained severe ache of the back with incomplete gait due to sensory impairment. Her ache disappeared after 2 months of continued administration of the present substance at a dose of 3 g/day as well as her sensory impairment. During the following 2 years, an improvement of subjective symptoms was observed, and now (3 years and 7 months after the commencement of the administration) she is healthy with a normal life.

Case 5: (Cancer of the stomach which metastasized to the liver)

A man of 61 years was examined as an outpatient complaining unpleasant feeling on the stomach and after diagnosed to be cancer of the stomach he had a total gastrectomy. After one and a half year, a tumour was found in the right costal margin and he was diagnosed to be the recurrence of cancer on the liver by scintigraphy. After 4 weeks of the beginning of administration of the present substance at a dose of 3 g/day, a reduction in size of the tumour and in ascites were found with the reduction of the abdominal girth of from 81 to 71 cm. Moreover, the relief of jaundice and the distinct reduction of serum bilirubin were observed.

Case 6: (Medulloblastoma)

A boy of 12 years had an operation for medulloblastoma 6 years ago and a tumour was recognized in his cerebellum. In spite of a radiation therapy, a metastasis to the spinal cord was observed. After 2 weeks of the beginning of administration of the present substance he became to begin phonation some times, before that he was in the state of half-coma or of somnolentia. His conditions were improved to the state of indicating the numbers of his fingers in a voice.

What is claimed is:

1. An antitumor agent suitable for oral administration to a mammal having cancer, said antitumor agent being capable of retarding the growth of said cancer, which comprises an effective amount of a protein-bound polysaccharide obtained by extraction of a mycelium or fruit body of a Coriolus of Polyporaceae of Basidiomycetes and having a molecular weight within the range of 5,000 to 300,000 as measured with ultracentrifugation and which gives a positive color reactions characteristic of saccharides with α-naphthol-sulfuric acid, indolesulfuric acid, anthrone-sulfuric acid, phenol-sulfuric acid, and tryptophane-sulfuric acid, a positive ninhydrin color reaction characteristic of amino acids after hydrochloric acid hydrolysis and a positive color reaction in the Lowry-Folin test characteristic of peptide linkage, said protein-bound polysaccharide having absorption regions, as measured by proton nuclear magnetic resonance spectra, at 0.9±0.1 ppm, 1.2±0.1 ppm, 2.0±0.1 ppm, 4.5±0.1 ppm and 4.7±0.1 ppm, with broad absorption at 3.0–4.4 ppm, said protein-bound polysaccharide having a polysaccharide portion/protein portion ratio within the range of 55/45 to 95/5 provided that the proton strength of the protein portion is at 0.5–2.5 ppm and that of the polysaccharide portion is at 2.5–6.0 ppm, and said polysaccharide portion being composed of β-glucan, showing no absorption attributed to α-glucan at 4.9–6.0 ppm, said protein portion being composed of aspartic acid, threonine, serine, glutamic acid, proline, glycine, alanine, cysteine, valine, methionine, isoleucine, leucine, tyrosine, tryptophane, phenylalanine, lysine, histidine and arginine, said polysaccharide being present in an amount sufficient to retard the growth of cancer.

2. A method of treating a cancer in a mammal which comprises administering to a mammal having a cancer an effective amount of a protein-bound polysaccharide obtained by extraction of a mycelium or fruit body of a Coriolus of Polyporaceae of Basidiomycetes and having a molecular weight within the range of 5,000 to 300,000 as measured with ultracentrifugation and which gives a positive color reactions characteristic of saccharides with α-naphthol-sulfuric acid, indolesulfuric acid, anthrone-sulfuric acid, phenolsulfuric acid, and tryptophane-sulfuric acid, a positive ninhydrin color reaction characteristic of amino acids after hydrochloric acid hydrolysis and a positive color reaction in the Lowry-Folin test characteristic of peptide linkage, said protein-bound polysaccharide having absorption regions, as measured by proton nuclear magnetic resonance spectra, at 0.9±0.1 ppm, 1.2+0.1 ppm, 2.0±0.1 ppm, 4.5±0.1 ppm and 4.7±0.1 ppm, with broad absorption at 3.0–4.4 ppm, said protein-bound polysaccharide having a polysaccharide portion/protein portion ratio within the range of 55/45 to 95/5 provided that the proton strength of the protein portion is at 0.5–2.5 ppm and that of the polysaccharide portion is at 2.5–6.0 ppm, and said polysaccharide portion being composed of β-glucan, showing no absorption attributed to α-glucan at 4.9–6.0 ppm, said protein portion being composed of aspartic acid, threonine, serine, glutamic acid, proline, glycine, alanine, cysteine, valine, methionine, isoleucine, leucine, tyrosine, tryptophane, phenylalanine, lysine, histidine and arginine, said effective amount being sufficient to retard the growth of said cancer.

3. A method of claim 1 wherein said cancer is mammary cancer.

4. A method of claim 1 wherein said cancer is a gastro-intestinal cancer.

5. A method of claim 4 wherein said cancer is a cancer of the esophogus.

6. A method of claim 4 wherein said cancer is stomach cancer.

7. A method of claim 4 wherein said cancer is cancer of the large colon.

8. A method of claim 2 wherein said cancer is a brain tumor.

9. A method of claim 2 wherein said cancer is lung cancer.

10. A method of claim 2 wherein said polysaccharide is administered orally. Q 11. A method of claim 2 wherein said polysaccharide is administered intraperitoneally.

12. A method of retarding the recurrence of cancer in a patient whose cancerous growth has been removed by surgery which comprises administering to said patient a prophylactically effective amount of a protein-bound polysaccharide obtained by extraction of a mycelium or fruit body of a Coriolus of Polyporaceae of Basidiomycetes and having a molecular weight within the range of 5,000 to 300,000 as measured with ultracentrifugation and which gives a positive color reactions characteristic of saccharides with α-naphthol-sulfuric acid, indolesulfuric acid, anthronesulfuric acid, phenol-sulfuric acid, and tryptophane-sulfuric acid, a positive ninhydrin color reaction characteristic of amino acids after hydrochloric acid hydrolysis and a positive color reaction in the Lowry-Folin test characteristic of peptide linkage, said protein-bound polysaccharide having absorption regions, as measured by proton nuclear magnetic resonance spectra, at $0.9\pm0.1$ ppm, $1.2\pm0.1$ ppm, $2.0\pm0.1$ ppm, $4.5\pm0.1$ ppm and $4.7\pm0.1$ ppm, with broad absorption at 3.0–4.4 ppm, said protein-bound polysaccharide having a polysaccharide portion/protein portion ratio within the range of 55/45 to 95/5 provided that the proton strength of the protein portion is at 0.5–2.5 ppm and that of the polysaccharide portion is at 2.5–6.0 ppm, and said polysaccharide portion being composed of β-glucan, showing no absorption attributed to α-glucan at 4.9–6.0 ppm, said protein portion being composed of aspartic acid, threonine, serine, glutamic acid, proline, glycine, alanine, cysteine, valine, methionine, isoleucine, leucine, tyrosine, tryptophane, phenylalanine, lysine, histidine and arginine, said prophylactially effective amount being sufficient to retard the reappearance of said cancer.

* * * * *